United States Patent [19]

Widder

[11] Patent Number: 5,611,342
[45] Date of Patent: Mar. 18, 1997

[54] METHOD OF COMPUTER TOMOGRAPHY IMAGING THE GASTROINTESTINAL TRACT AND SURROUNDING UPPER ABDOMINAL TISSUES AND ORGANS USING AN ORALLY ADMINISTERED LOW DENSITY CONTRAST MEDIUM

[75] Inventor: Kenneth J. Widder, Rancho Santa Fe, Calif.

[73] Assignee: Molecular Biosystems, Inc., San Diego, Calif.

[21] Appl. No.: 483,648

[22] Filed: Jun. 7, 1995

Related U.S. Application Data

[63] Continuation of Ser. No. 196,965, Feb. 15, 1994, abandoned.
[51] Int. Cl.$^6$ ............................................. A61B 6/00
[52] U.S. Cl. ........................... 128/654; 424/9.4; 436/173
[58] Field of Search ........................... 128/654, 653.4; 424/4, 5, 9, 9.42, 9.43, 9.45, 9.4; 436/173

[56] References Cited

U.S. PATENT DOCUMENTS

| | | | |
|---|---|---|---|
| 4,243,652 | 1/1981 | Francis | 128/654 |
| 4,615,879 | 10/1986 | Runge et al. | 424/9 |
| 5,004,835 | 4/1991 | Blaszkiewicz et al. | |
| 5,019,370 | 5/1991 | Jay et al. | |
| 5,019,371 | 5/1991 | Lin et al. | |
| 5,069,216 | 12/1991 | Groman et al. | 128/653.4 |
| 5,073,362 | 12/1991 | Blaszkiewicz et al. | |
| 5,075,502 | 12/1991 | Kneller et al. | |
| 5,183,654 | 2/1993 | Speck et al. | |
| 5,191,120 | 3/1993 | Kneller et al. | |
| 5,204,086 | 4/1993 | Wille | |
| 5,232,685 | 8/1993 | Speck et al. | |
| 5,233,995 | 8/1993 | Yuddleson et al. | |
| 5,542,605 | 8/1994 | Illig | 424/5 |

FOREIGN PATENT DOCUMENTS

| | | |
|---|---|---|
| 0245019 | 11/1987 | European Pat. Off. |
| 8503004 | 7/1985 | WIPO ........................... 424/5 |
| WO92/17514 | 10/1992 | WIPO |
| 95/32005 | 11/1995 | WIPO |
| 95/32006 | 11/1995 | WIPO |

OTHER PUBLICATIONS

Makino et al., Stomach Diagnosis with Universal Gyroscopic X–ray TV Apparatus, Model DT–UG, Toshiba Review, No. 7, Jun. 1972, pp. 13–17.

Canada et al., "Use of urokon (sodium–3–acetylamino–2,4,6–triiodo–benzoate) in roentgen study of the gastrointestinal tract" *Radiology* (1955) 64:867–873.

Fisher, "Normal colon wall thickness on CT" *Radiology* (1982) 145:415–418.

Lee et al., eds., *Computed Body Tomography with MRI Correlation*, Second Edition, Raven Press, New York, Chap. 3, pp. 44–46.

Marks et al., "Intestinal pseudotumors: a problem in abdominal tomography solved by directed techniques" *Gastrointest. Radiol.* (1980) 5:155–160.

Garrett et al., "Oral contrast agents in CT of the abdomen" *Radiology* (1984) 153:545–546.

Oral Presentation of American Roentgen Ray Society Meeting summarized in *Diagnostic Imaging* article entitled "Water–contrast CT offers better view of upper GI tract" (Jan. 1994) p. 22.

Baldwin, "Computed tomography of the pancreas: negative contrast medium" *Radiology* (1978) 128:827–828.

Raptopoulos et al., "Fat–density oral contrast agent for abdominal CT" *Radiology* (1987) 164(3):653–656.

Raptopoulos et al., "Imaging of the bowel wall computed tomography and fat density oral–contrast agent in animal model" *Investigative Radiology* (1986) 21(11):847–850.

Lembcke et al., "Role of gastrointestinal transit in the delay of absorption by viscous fibre (guar)" *Hepato–gastroenterol.* (1984)31:183–186.

Bolondi et al., "Measurement of gastric emptying time by real–time ultrasonography" *Gastroenterology* (1985) 89:752–759.

Minami et al., "The physiology and pathophysiology of gastric emptying in humans" *Gastroenterology* (1984) 86:1592–1610.

Hunt, "Does calcium mediate slowing of gastric emptying by fat in humans" *Gastrointestinal Liver Physiology* (1983) 7:G89–G94.

Nyman et al., "E–Z–CAT. An oral contrast medium for use in computed tomography" *Acta Biologica Diagnosis* (1984) 25:121–124.

Zwaan et al., "Normale wandstärke und tumoröse wandveränderungen des gastrointestinaltraktes in der computertomographie" *Fortschr. Röntgenstr.* (1991) 155(5):423–427.

*Primary Examiner*—Marvin M. Lateef
*Assistant Examiner*—Brian L. Casler
*Attorney, Agent, or Firm*—Morrison & Foerster

[57] ABSTRACT

A method for enhanced CT imaging of the tissues defining the upper gastrointestinal tract and the upper abdominal organs wherein the upper gastrointestinal tract is filled with a chemically defined low density CT contrast agent solution having a prolonged gastric emptying time, thus causing the lumen of the upper gastrointestinal tract to appear less dense than the gastrointestinal tract walls and upper abdominal organ.

18 Claims, No Drawings

METHOD OF COMPUTER TOMOGRAPHY IMAGING THE GASTROINTESTINAL TRACT AND SURROUNDING UPPER ABDOMINAL TISSUES AND ORGANS USING AN ORALLY ADMINISTERED LOW DENSITY CONTRAST MEDIUM

This application is a continuation of application Ser. No. 08/196,965, filed on Feb. 15, 1994 now abandoned.

TECHNICAL FIELD

This invention is in the field of x-ray, especially computerized tomography (CT), imaging of the human body for diagnostic purposes. More particularly, it relates to methods of imaging the tissue defining the stomach, tissues and organs proximal thereto, and other organs and structures in the upper abdominal cavity. The imaging method of the present invention relates to the use of a low density contrast medium which fills and distends the lumen of the gastrointestinal tract to distend the lumen and provide improved visualization of the relatively more dense surrounding structures and tissues while at the same time reducing imaging artifacts.

BACKGROUND

In the past several decades, advances have been made in various methodologies which allow the visualization of internal organs and tissue structures using non-invasive techniques. In particular, the development of advanced radiographic techniques such as CT allow for the differentiation of soft tissue structures with density differences as small as 0.5%, whereas with conventional x-ray techniques such differentiation was not possible.

One of the most significant advances in conventional x-ray was the development of water-soluble iodine containing radiographic contrast media. Canada reported the use of an orally ingested contrast media which was used for imaging of the gastrointestinal tract (W. J. Canada (1955) Radiology 64:867–873.) The radio-opacity of the iodine made the gastrointestinal tract lumen appear bright white in the x-ray image. This allowed for better visualization of obstructions and perforations.

Both orally ingested barium sulfate suspensions and water soluble iodine containing contrast media have also been used as positive (high density) contrast media for CT applications. These positive oral contrast agents provide valuable information about the gastrointestinal lumen in which they are localized during imaging. However, their opacity in the CT image can diminish the ability to evaluate wall structures and surrounding tissues and organs. Of particular importance, is the inability to correctly determine gastrointestinal wall thickness as an indicator of possible disease in the presence of a positive contrast agent which obscures wall definitions (Fisher, Radiology (1982) 145:415–418.) Also, when a positive contrast agent is employed, it can obscure the imaging of adjacent calcifications and the ability to carefully evaluate the stomach and duodenum. (Lee et al., eds., Computed Body Tomography with MRI Correlation, Second Edition, Raven Press, New York, Chapter 3, pp. 44–46).

In some cases, the use of positive contrast agents can lead to a false positive diagnosis of pathologic processes, sometimes referred to as pseudotumors (Marks et al., Gastrointestinal Radiology (1980) 5:155–160.) Further problems which arise when using either barium sulfate suspensions or water-soluble iodinated oral contrast agents can be due to the inability of these agents to mix well with the contents of the gastrointestinal tract thus giving rise to a heterogeneous opacification and artifacts in the CT image (Garret et al., Radiology (1984) 153:545–546).

In the absence of an orally administered contrast agent, imaging of the upper abdomen can also be affected by the contents of the gastrointestinal tract, which may produce imaging artifacts. If the imaging densities of the heterogeneous gastrointestinal contents are similar to that of the surrounding tissues, the visualization of such tissues and organs proximal thereto can be obscured. In addition, the uneven distension of the colon due to the presence of normal intestinal contents (gas and stool) can further interfere with imaging.

One way in which to overcome the difficulties associated with positive contrast agents or the absence of a contrast agent is to introduce a low density contrast agent into the gastrointestinal tract. Alger has reported that for upper gastrointestinal imaging, water in combination with intravenous glucagon (an anti-peristaltic agent) can be given to patients prior to CT examination to enhance the visualization of the area (Oral presentation of American Roentgen Ray Society Meeting summarized in Diagnostic Imaging, January 1994, page 22.) However, the use of water has been reported to lead to the production of imaging artifacts (Baldwin, Radiology (1978) 128:827–828.) Additionally, without concomitant intravenous administration of an anti-peristaltic agent such as glucagon, the rapid gastric emptying of water would not allow for full distension of the stomach.

Many investigators have described the use of low-density contrast media for CT examinations. The radiodensity of matter is often expressed in terms of its Hounsfield Units (HU), which is a measure of the relative absorption of CT x-rays by matter. Dense bone has a density of 1000 HU, whereas water has a density of 0 HU and air has a value of –1000 HU. In general, the term "low-density" is used to refer to contrast media with a low or negative HU, i.e. less than about 100 HU, preferably less than 10 HU, and most preferably less than 0 HU.

Baldwin reported the administration of low density oily contrast media for CT of the pancreas. However, because of associated cramps and diarrhea, a dose of 4 ounces was suggested, which would not be enough to sufficiently fill the stomach and/or gastrointestinal lumen. (Baldwin, Radiology (1978) 128:827–828.)

Raptopoulos et al., has described the use of a corn oil emulsion as a low density contrast agent (Radiology (1987) 164 (3) :653–656. At a dosage amount of between 200–500cc, 18% of the patient group complained of nausea, vomiting, cramps or diarrhea. Another disadvantage with the use of polyunsaturated fat-based low density contrast agents is their absorption by the gastrointestinal tract (Raptopoulos, Investigative Radiology (1986) 21(11):847–850.) In European Patent Application 0 245 019A2, Raptopoulos has described the use of oil-in-water emulsions suspended in an aqueous isotonic solution which demonstrate improved homeostasis.

A similar approach has been described in PCT WO92/17514. Therein, microspheres are prepared from biocompatible synthetic polymers to contain internal cavities filled with gas. Because of the presence of gas, these microspheres have a lower radiodensity than water. These microspheres are then suspended in an aqueous medium at concentrations that generate a contrast medium with a HU less than –30.

The preparation of such microspheres necessitates multi-step methodologies involving volatile liquids. In addition, the microspheres in the preferred size ranges would not be stable upon storage in aqueous solution thus requiring dry storage and mixing with a carrier liquid prior to use.

The present invention describes a method of CT imaging of the abdominal region using low density contrast agents consisting of aqueous solutions of biocompatible materials which are stable, have a density (in Hounsfield Units) essentially the same or less than that of water, and are capable of filing and distending the stomach.

DISCLOSURE OF THE INVENTION

The invention is a method of CT imaging of tissue defining the upper gastrointestinal tract and organs in the upper abdomen comprising:

a) introducing a sufficient volume of a low density CT contrast agent solution of a biocompatible material into the stomach to substantially fill and distend the stomach, said solution having a greater gastric emptying time than water;

b) applying an x-ray beam to the upper abdomen while said solution is present in the upper gastrointestinal tract, said x-ray beam passing through the solution and being differentially absorbed by said tissue and said organs; and c) forming a CT image from said beam.

MODES FOR CARRYING OUT THE INVENTION

The solutions of the present invention provide low density biocompatible media that have a prolonged (relative to water) transit time through the upper gastrointestinal tract. Low density permits image enhancement. Prolonged transit time gives the radiologist more time to perform the imaging procedure and reduces motion artifacts. Thus, the role of the biocompatible material is to increase the gastric emptying time of the medium without unduly increasing its density. Preferably, the material either has no significant affect on density (i.e., the density of the solution in essentially the same as water) or reduces the density to below that of water.

Any variety of water soluble or suspendible biocompatible materials which provide the desired low density and are capable of increasing gastric emptying time and forming a stable solution may be employed in the invention method. The term "biocompatible" denotes the absence of interaction of the material(s) with the fluids, tissues, organs and structures of the body to cause adverse or toxic reactions. The term "solution" is meant to refer to both a true solution and a suspension or dispersion of biocompatible material. When the biocompatible material is suspended or dispersed, it is in the form of homogenous solid particles which are essentially free of entrapped gas (i.e., comprise less than 5% v/v entrapped gas). The term "solid" is intended to include true solids and gels.

Materials suitable for the present invention include polymeric and nonpolymeric compounds. In addition, they may be synthetic or naturally occurring. The term polymeric is used to refer to a compound comprised of two or more repeating monomeric units. The term synthetic may refer to both synthesized non-naturally occurring materials as well as naturally occurring materials which have been derivatized or chemically modified. In addition to the biocompatible material(s), the solution may optionally include anti-microbial agents, anti-gas agents, wetting agents, flavoring agents and coloring agents.

As indicated, the present invention employs solutions which exhibit an increased gastric retention time when compared to water. Gastric emptying time of a solution is a function of the rate at which the contents of the stomach empty and can be expressed as the time it takes for the contents of the stomach to empty into the small bowel. Ways of measuring gastric emptying time are known in the art (see, for example, B. Lembcke, et al., Hepato-gastroenterology (1984) 31:183–186; L. Bolondi et al. Gastroenterology (1985) 89:752–759). The solutions of the present invention exhibit a gastric emptying time of greater than 20 minutes, preferably 30 minutes to 45 minutes, in the absence of parenteral coadministration of antiperistaltic agents such as glucagon or butylscopolamine bromide. An emptying time of greater than 20 minutes is preferred for upper gastrointestinal tract imaging to enable the radiologist to perform part of the x-ray exam while the medium is present in the stomach. During the examination process, which may take one half to one hour, and depending on the nature and extent of the examination necessary, the radiologist can image the upper gastrointestinal tract as well as surrounding upper abdominal tissues and organs.

The rate of gastric emptying is influenced by the contents of the stomach. Minami et al. (Gastroenterology (1984) 86:1592–1610) describe several factors that increase gastric emptying as being high osmolality, pH, the presence of certain amino acids such as L. tryptophan, the presence of fats such as $C_{10}$ to $C_{18}$ fatty acids, and nutritive density. Interaction of these substances with specific receptors in the small bowel is speculated to be the basis for this effect.

The relatively long gastric emptying time of the medium described herein for imaging of the upper gastrointestinal tract may be achieved by increasing osmolality, acidity, caloric content, viscosity and/or the inclusion of other solutes such as amino acids, fatty acids, glycerides (including mono-, di- and triglycerides), and agents that bind calcium ions. Fatty acids and agents that bind calcium ions at gastric pHs are known in the art (see, for example, J. N. Hunt, Gastrointest. Liver Physiol. (1983) 7:G89–G94). Preferably the solution is hyperosmolar, i.e., has an osmolality above about 300 millimoles per kilogram (mM/kg). The osmolality of a solution is defined as the total number of solute particles dissolved in one kilogram of solvent, and it is independent of physical properties of the particles such as size and density.

Examples of solutes which may be used either alone or in combination to make hyperosmolar solutions are modified polysaccharides such as polydextrose, modified starches such as maltodextrin, corn syrup, glycerin and nonpolymeric saccharides such as aldoses, ketoses, erythrose, threose, ribose, arabinose, xylose, lyxose, allose, altrose, glucose, mannose, idose, galactose, talose, erythrulose, ribulose, xylulose, psicose, fructose, sorbose, tagatose, glucuronic acid, gluconic acid, glucaric acid, galacturonic acid, mannuronic acid, glucosamine, galactosamine and neuraminic acid.

Although the concentration of the particular solute(s) used to increase osmolality will depend on its (their) molecular weight, typical concentrations will normally be in the range of 10% to 50% w/v.

Hydrocolloids are examples of biocompatible materials that may be used to increase the viscosity of the solution. A hydrocolloid should be selected which can be dissolved or dispersed in water to form either a true solution or a stable dispersion. Hydrocolloids which are water-soluble or hydratable are preferred, and can be used either alone or in combination. Examples of such hydrocolloids include, but are not limited to, naturally occurring polymers such as arabians, fructans, fucans, galactans, galacturonans, glucans, mannans, xylans, levan, fucoidan, carragheenan, galactocarolose, pectic acid, amylose, pullulan, glycogen, amylopectin, pectin, cellulose, dextran, pustulan, chitin, agarose, keratin, chondroitin, dermatan, hyaluronic acid, alginic acid, xanthan gum, guar gum, agar and acacia; and synthetic polymers such as the following: cellulose derivatives such as methylcellulose, carboxymethylcellulose, hydroxymethylcellulose, hydroxypropylmethylcellulose, and methoxycellulose; polyethylenes such as polyethylene glycol and polyoxyethylene; polypropylenes such as polypropylene glycol; polyurethanes; polyesters such as polylmethylmethacrylate; pluronic acids; polyvinyls such as polyvinyl alcohol and polyvinylpyrrolidone.

The suitability of a hydrocolloid for the purpose of increasing viscosity for use in the present invention can be determined by preparing admixtures with water within the range from 0.5% to 8% by weight, and measuring the solution viscosity using known methods. The amount of the hydrocolloid used should provide a solution viscosity in the range of 200 to 800 centipoise (cp) at 25° C. and preferably from 300 to 600 cp. For example, pectin can be employed in amounts of 2% to 5% by weight. In one embodiment, the pectin percent is from 3% to 4% and provides viscosities of from 520 to 575 cp.

Suitable hydrocolloids and their viscosities are shown in the Table 1 below:

TABLE 1

Hydrocolloid Solution Viscosities

| Solution | Manufacturer | Concentration % (w/v) | Viscosity at 20–25° C. (cp) |
|---|---|---|---|
| Sterile Water | Arrowhead | — | — |
| Pectin LM-32 | TIC Gums, Inc. | 3.50 | 524 |
| Genu Pectin USP L-200 | Hercules, Inc. | 3.75 | 571 |
| Xanthan PH (xanthan gum) | TIC Gums, Inc. | 0.51 | 426 |
| Keltrol T (sodium alginate) | Kelco | 0.80 | 434 |
| Kelgin F (sodium alginate) | Kelco | 1.46 | 449 |
| Kelgin MV (sodium alginate) | Kelco | 1.40 | 551 |
| Keltone HV (sodium alginate) | Kelco | 1.16 | 541 |
| Colloid 602 (propylene glycol alginage) | TIC Gums, Inc. | 1.55 | 498 |
| Colloid 775 (carageenan) | TIC Gums, Inc. | 1.13 | 384 |
| Colloid 720 (carageenan) | TIC Gums, Inc. | 1.13 | 384 |

The solutions may be made by adding the solute and other additives (if present) to water, optionally with mixing and heating to facilitate complete solubilization of the solute and additives. The solution may then be degassed, such as by subjecting the solution to vacuum, and placed in appropriate packaging. It should be noted that the solutions of the invention are chemically defined, meaning that their chemical compositions are predetermined, known, and reproducible.

In use the CT contrast medium is introduced into the stomach by ingestion or intubation, preferably the former, of a fasting patient (either a human or other mammalian animal). The volume of solution introduced should be sufficient to substantially fill and distend the stomach (typically 100 to 1000 cc, preferably 250 to 500 cc for adults humans and 100 to 300 cc for children) and displace the contents therefrom. A CT examination of the upper abdomen is then performed with conventional equipment to produce an image of the upper gastrointestinal tract and upper abdominal organs (pancreas, spleen, portions of kidney). As indicated, due to the presence of the low-density solution in the upper gastrointestinal tract, the radiologist is able to obtain enhanced images of the gastrointestinal tract walls and adjacent abdominal organs. Because of its low density, the solution enhances the imaging of the surrounding structures. The images may be used to detect or monitor disease or other abnormalities in the tissue or organ being visualized.

In order to enhance the contrast of the area being imaged which is proximal to the lumen of the gastrointestinal tract containing the low density contrast agent, the method of the present invention optionally covers the concomitant parenteral (e.g. intravenous) administration of a positive CT agent, i.e. one that absorbs x-rays and hence appears bright in the CT image. Suitable CT agents are well known in the art and may include the agents described in the following U.S. Pat. Nos. which are incorporated herein by reference in their entirety: 5,204,086; 5,233,995; 5,232,685; 5,183,654; 5,190,120; 5,073,362; 5,004,835; 5,019,370; 5,019,371; and 5,075,502.

The following examples further illustrate aspects of this invention. These examples are not intended to limit the invention in any manner.

EXAMPLE 1

Sample Preparation and Osmolality Determination

One liter batches of each sample were prepared according to the formulations described in Table 1 below by adding the ingredients to water and mixing to homogeneity. The solution osmolality was adjusted to the desired range by diluting with water containing the appropriate concentration of preservative. Each sample was then degassed in a vacuum chamber which was maintained at about 30 mm/Hg for approximately four hours.

The Osmolalies of the solutions in mmol/kg were determined using a Wescor (Logan, Utah) Vapor Pressure Osmometer. The addition of solute particles to a solvent changes the free energy of the solvent molecules, and as a result, the colligative properties (i.e., vapor pressure, freezing point, boiling point) of a single solvent solution change linearly in proportion to the concentration of solute particles. The Wescor Vapor Pressure Osmometer 5500 measures the osmolality of a solution indirectly by measuring the dew point temperature depression which has a linear response between 100 and 2000 mmol/kg.

Before the osmolality of the samples was measured, the Wescor Vapor Pressure Osmometer was warmed up for at least 90 minutes. The instrument was calibrated using the Wescor ampule standards of 290 to 1000 mmol/kg. The slope of the calibration curve was adjusted by first setting the instrument to read 1000 mmol/kg with the 1000 mmol/kg standard; the offset (zero intercept) was then adjusted with the 290 mmol/kg standard.

After the Wescor Vapor Pressure Osmometer 5500 had been calibrated, a ten microliter sample of the test solution was pipetted onto a small solute-free paper disc which was then inserted into the sample chamber. The chamber was heated to 37° C. The observed dew point temperature depression was converted to osmolality and the results are reported below in Table 2.

TABLE 2

Osmolality Results

| Solution | Ingredients | Concentration | Osmolality (mmol/kg) |
|---|---|---|---|
| Polydextrose | Polydextrose | 25% w/w | 589 + 11 |
| | Potassium | 0.1% w/w | |
| | Sorbate | 0.1% w/w | |
| | Sodium Benzoate | N/A | |
| | Water for Cell Cul. | | |
| Maltodextrin | Maltrin M-150 | 48.5% w/v | 740 + 3 |
| | Sorbic Acid | 0.1% w/v | |
| | Benzoic Acid | 0.1% w/v | |
| | Water for Cell Cul. | N/A | |
| Corn Syrup | Globe cs 1137NF | 15.75% v/v | 521 + 6 |
| | Sorbic Acid | 0.1% w/v | |
| | Benzoic Acid | 0.1% w/v | |
| | Water for Cell Cul. | N/A | |
| Glycerin | Glycerin | 6.6% w/v | 936 + 2 |
| | Sorbic Acid | 0.1% w/v | |
| | Benzoic Acid | 0.1% w/v | |
| | Water for Cell Cul. | N/A | |

EXAMPLE 2

Determination of Gastric Retention Time

Gastric retention time of maltodextrin and polydextrose solutions were determined as follows: After fasting for 8–12 hours, 250 mL of either solution was ingested. Ultrasound imaging was performed in the upright standing position throughout the procedure.

B-mode ultrasound imaging of the gastrointestinal tract and surrounding tissues and organs was done with a Toshiba 5MHz curved array transducer (Toshiba PVF-575MT) coupled to a Toshiba sonolayer Ultrasound instrument with SSA-270A version 7.01 software. Images were videotaped immediately prior to ingestion of the test solutions (time 0) and at five minute intervals thereafter. DgC settings were optimized to give a clear image of the gastrointestinal tract, in particular the stomach, and adjacent tissues/organs with depth settings of either 10 or 12 cm. From the videotaped images, estimates of the stomach size were obtained by capturing a longitudinal image of the organ and measuring the area within the stomach lining. The value determined for each time point was normalized by division by the time 0 value. These data are summarized in Table 3 below.

TABLE 3

Effect of Contrast Agents on Stomach Size

| | TIME (MINUTES) | | | | | | |
|---|---|---|---|---|---|---|---|
| | 0 | 5 | 10 | 15 | 20 | 25 | 30 |
| Water | 1.00 | 0.89 | 0.93 | 0.92 | | | |
| 50% (w/v) Maltodextin | 1.00 | 1.89 | 1.75 | 1.69 | 1.73 | 1.62 | 1.88 |
| 25% (w/v) Polydextrose | 1.00 | 2.28 | 2.56 | 2.64 | 2.55 | 1.97 | 1.79 |

The data in Table 3 demonstrate that the polydextrose and maltodextrin solutions have a gastric emptying time of greater than 20 minutes. With either solution, an immediate apparent increase in stomach size was observed which was maintained for at least 20 minutes. In comparison, when the same volume of water was ingested, no increase in stomach dimensions was observed due to the fact that the water is rapidly clearing from the stomach.

EXAMPLE 3

In-vitro Analysis of Radiodensity

Transparent amber containers, which exhibit minimal absorption of x-ray, were completely filled with the following solutions: 12.5% polydextrose, 25% polydextrose or sterile water. The Hounsfield Units of the solutions were determined in a GE 9800 Advantage (General Electric Medical systems, Waukesha, Wis.) CST scanner calibrated internally according to manufacturer specifications. A single scan of each solution was taken and stored on videotape for processing. A region of interest (1 cm diameter) in the scan of each solution was chosen and the HU was determined accordingly. The results are as follows:

TABLE 4

| SOLUTION | HU |
|---|---|
| 12.5% (w/v) Polydextrose | 54.2 |
| 25% (w/v) Polydextrose | 99.3 |
| Sterile Water | 2.0 |

EXAMPLE 4

In-Vivo CT Imaging

CT imaging can be carried out by standard procedures using commercially available equipment. The x-ray beam energy is typically 120KeV although dual energy seam systems are available. X-ray CT is an inherently two-dimensional imaging method that acquires transaxial images of any region of the human body, provided that region is located within the x-ray beam/detector gantry. Conventional CT scanners use fixed parameters for slice thickness; the in-plane resolution can be adjusted within pre-determined parameters set by the manufacturer (e.g., 256×256 or 512 pixel resolution and scan time—which is a function of the resolution). Spiral or helical scanning CT units allow for more options of slice thickness and typically have shorter scan times (about 1 second/slice). The following general procedure is illustrative of the method using a conventional CT scanner.

Stomach—Upper GI Tract

The subject is placed supine on the CT scanner patient platform ("couch"). An initial alignment using the positioning system of the scanner and external anatomic reference points on the subject is done. A "scout" image is done to determine if the subject is properly located within the CT gantry; if not, the subject is repositioned by remotely controlling the travel of the patient platform to obtain the desired location (this is repeated until desired alignment is achieved).

Typically, a series of precontrast images are obtained. Following this step, the subject ingests 250–500 mL of the contrast medium over a two minute period. (Subject may need to sit to ingest and be repositioned in CT gantry.) The CT examination of the upper abdominal region is then performed while the contrast medium is present in the stomach and upper gastrointestinal region.

Modifications of the above described modes for carrying out the invention that are obvious to those of skill in the fields of radiography, radiographic contrast media and related fields are intended to be within the scope of the following claims.

I claim:

1. A method of computerized tomography (CT) imaging of upper gastrointestinal tract and upper abdominal organs of a subject comprising:
   a) introducing a low density CT contrast agent solution of a biocompatible material into the subject's stomach, said solution being essentially free of entrapped gas and being a true solution of said biocompatible material;
   b) allowing said true solution to:
      i) substantially fill and distend the subject's stomach;
      ii) displace any heterogeneous contents therefrom; and
      iii) remain in the stomach longer than an equal volume of water;
   c) applying an x-ray beam to the upper abdominal organs while said solution is present in the upper gastrointestinal tract, said x-ray beam passing through the solution and being differentially absorbed by said tissue and said organs; and
   d) forming a CT image from said beam unobscured by any heterogeneous gastrointestinal contents.

2. The method of claim 1 wherein said volume is 100 to 1000 cc.

3. The method of claim 2 wherein the method is performed on an adult human and said volume is 250 to 500 cc.

4. The method of claim 1 wherein the biocompatible material is a naturally occurring polymer or a synthetic polymer.

5. The method of claim 1 wherein the biocompatible material is a modified starch or a synthetic polysaccharide.

6. The method of claim 1 wherein the biocompatible material is maltodextrin or polydextrose.

7. The method of claim 1 wherein the gastric emptying time of the solution is greater than about 20 minutes.

8. The method of claim 1 wherein the gastric emptying time is about 30 to about 45 minutes.

9. The method of claim 1 wherein the biocompatible material increases one or more of the osmolality, acidity, caloric content or viscosity of the solution, thereby causing the solution to have said gastric emptying time.

10. The method of claim 1 wherein the biocompatible material is an amino acid, fatty acid, glyceride or calcium binding agent that causes the solution to have said gastric emptying time.

11. The method of claim 10 wherein the biocompatible material is a $C_{10}$ to $C_{18}$ fatty acid.

12. The method of claim 1, further comprising the step of intravenously administering a positive CT agent.

13. A method of computerized tomography (CT) imaging of tissue defining the upper gastrointestinal tract and organs in the upper abdomen comprising:
   a) introducing a low density CT contrast agent solution of a biocompatible material into the stomach, said solution being essentially free of entrapped gas and being a homogeneous suspension or dispersion of homogeneous solid particles of said biocompatible material;
   b) allowing said homogeneous suspension to:
      i) substantially fill and distend the subject's stomach;
      ii) displace any heterogeneous contents therefrom; and
      iii) remain in the stomach longer than an equal volume of water;
   c) applying an x-ray beam to the upper abdomen while said solution is present in the upper gastrointestinal tract, said x-ray beam passing through the solution and being differentially absorbed by said tissue and said organs; and
   d) forming a CT image from said beam unobscured by any heterogeneous gastrointestinal contents.

14. The method of claim 13 wherein said volume is 100 to 1000 cc.

15. The method of claim 14 wherein the method is performed on an adult human and said volume is 250 to 500 cc.

16. The method of claim 13 wherein the gastic emptying time of the solution is greater than about 20 minutes.

17. The method of claim 13 wherein the gastric emptying time is about 30 to 45 minutes.

18. The method of claim 13 wherein a positive computer tomography contrast agent is administered intravenously concomitantly with the administration of the solution.

* * * * *